United States Patent
Mangaud

(10) Patent No.: US 10,362,370 B2
(45) Date of Patent: Jul. 23, 2019

(54) DEVICE FOR CREATING ENHANCED VIDEOS

(71) Applicant: PIQ, Neuilly-sur-Seine (FR)

(72) Inventor: Cedric Mangaud, Suresnes (FR)

(73) Assignee: PIQ, Neuilly-sur-Seine (FR)

( * ) Notice: Subject to any disclaimer, the term of this patent is extended or adjusted under 35 U.S.C. 154(b) by 101 days.

(21) Appl. No.: 15/109,836

(22) PCT Filed: Jan. 5, 2015

(86) PCT No.: PCT/EP2015/050039
§ 371 (c)(1),
(2) Date: Jul. 6, 2016

(87) PCT Pub. No.: WO2015/101663
PCT Pub. Date: Jul. 9, 2015

(65) Prior Publication Data
US 2016/0330533 A1    Nov. 10, 2016

(30) Foreign Application Priority Data

Jan. 6, 2014  (CH) .......................................... 4/14

(51) Int. Cl.
*H04N 21/8549*   (2011.01)
*H04N 5/232*   (2006.01)
(Continued)

(52) U.S. Cl.
CPC ........... *H04N 21/8549* (2013.01); *A61B 5/11* (2013.01); *A61B 5/6824* (2013.01);
(Continued)

(58) Field of Classification Search
CPC ...... H04N 21/8549; H04N 5/232; H04N 7/18; H04N 21/42201; H04N 21/4223; G06T 11/00; H04Q 9/00; H04Q 2209/43; H04Q 2209/50; G08B 5/226; A61B 5/11; A61B 5/6824; A61B 5/6831; A61B 2562/0219; A61B 2562/028
(Continued)

(56) References Cited

U.S. PATENT DOCUMENTS

| 5,868,578 A | 2/1999 | Baum | |
|---|---|---|---|
| 2007/0280463 A1* | 12/2007 | Kouchri | H04Q 3/66 379/201.01 |
| 2008/0161060 A1* | 7/2008 | Yoshida | G06F 1/1616 455/566 |
| 2010/0107463 A1* | 5/2010 | Spiro | G02B 6/0086 40/546 |

(Continued)

OTHER PUBLICATIONS

International Search Report, dated Sep. 1, 2015, from corresponding PCT application.

*Primary Examiner* — Zaihan Jiang
(74) *Attorney, Agent, or Firm* — Young & Thompson

(57) ABSTRACT

A device for creating video sequences wherein a certain amount of data is added in order to better interpret and assess the video sequence. A typical use case is the following: a person with a Smartphone (or any other online terminal capable of carrying out a video recording) films a person (or object) that thereon has sensors (accelerometers, gyrometers, etc.) capable of communication. After processing, the data from the communication-capable sensors is transmitted via wireless communication to the Smartphone, that will aggregate same with the created video sequence. This is what is meant by "enhanced video".

5 Claims, 6 Drawing Sheets

Figure 1:
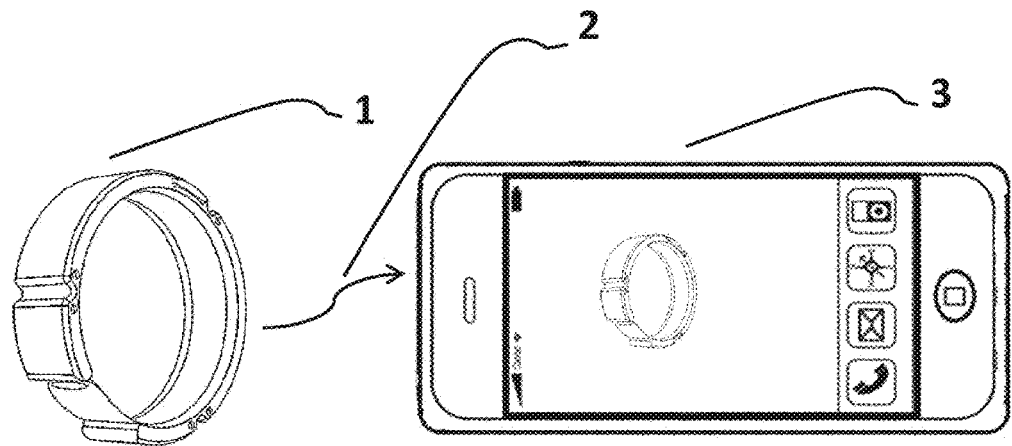

(51) Int. Cl.

| | |
|---|---|
| *H04N 7/18* | (2006.01) |
| *A61B 5/00* | (2006.01) |
| *H04N 21/4223* | (2011.01) |
| *G08B 5/22* | (2006.01) |
| *A61B 5/11* | (2006.01) |
| *G06T 11/00* | (2006.01) |
| *H04N 21/422* | (2011.01) |
| *H04Q 9/00* | (2006.01) |

(52) U.S. Cl.
CPC ............ *A61B 5/6831* (2013.01); *A61B 5/743* (2013.01); *G06T 11/00* (2013.01); *G08B 5/226* (2013.01); *H04N 5/232* (2013.01); *H04N 7/18* (2013.01); *H04N 21/4223* (2013.01); *H04N 21/42201* (2013.01); *H04Q 9/00* (2013.01); *A61B 2562/028* (2013.01); *A61B 2562/0219* (2013.01); *H04Q 2209/43* (2013.01); *H04Q 2209/50* (2013.01)

(58) Field of Classification Search
USPC ........................................................ 348/143
See application file for complete search history.

(56) References Cited

U.S. PATENT DOCUMENTS

| | | | |
|---|---|---|---|
| 2011/0071792 A1 | 3/2011 | Miner | |
| 2011/0082704 A1* | 4/2011 | Blum .................... | A61B 3/0285 705/2 |
| 2012/0151348 A1* | 6/2012 | Mital ............... | H04N 21/47205 715/727 |
| 2013/0066448 A1 | 3/2013 | Alonso | |
| 2013/0128022 A1* | 5/2013 | Bose ........................ | H04N 7/18 348/77 |
| 2013/0225309 A1* | 8/2013 | Bentley .................. | A63B 69/36 473/266 |
| 2013/0259446 A1* | 10/2013 | Sathish ................ | G11B 27/034 386/278 |
| 2013/0271602 A1* | 10/2013 | Bentley ..................... | H04N 7/18 348/143 |
| 2013/0324099 A1* | 12/2013 | Dgani ..................... | C08L 97/02 455/418 |
| 2013/0330054 A1 | 12/2013 | Lokshin | |
| 2014/0023201 A1* | 1/2014 | Daniels ................ | H04R 1/1091 381/74 |
| 2014/0115649 A1* | 4/2014 | Kim ..................... | H04N 21/234 725/116 |
| 2015/0019266 A1* | 1/2015 | Stempora ............... | G06Q 40/08 705/4 |

* cited by examiner

DEVICE FOR CREATING ENHANCED VIDEOS

TECHNICAL FIELD

The present invention concerns a device for creating "enhanced videos" sequences. The typical case of use is the following: a person equipped with a Smartphone (the Smartphone is a mobile cellular telephone provided in particular with a video camera, a screen and a digital processing unit, but it may also be any other terminal capable of making a video recording) films another person (or an object) who has sensors on her (accelerometer, rate gyro, thermometer, heart rate monitor, sensor of oxygen level in the blood, pressure sensor, etc.). After processing of the data from the sensors, these are sent via a wireless communication to the Smartphone which will aggregate them with the video sequence created. It is with this meaning that the term "enhanced video" is used. Below the term "connected sensors" is used in the case of a device (taken from a mechanical point of view in various forms: wrist band, parallelepiped, flat cylinder, etc.) comprising sensors as such, the analog and digital processing electronics as well as the radiofrequency part making it possible to perform wireless communication.

The device of the invention makes it possible to assist users in creating sequences that merge video and data from sensors.

STATE OF THE PRIOR ART

Devices for creating enhanced video are known: The company Amisco (http://www.sport-universal.com/) offers a system for creating enhanced videos based on the analysis of videos captured by video cameras during sports events. The elements coming from the analysis of the videos are then supplied to a database which may be exploited for various purposes including the creation of enhanced videos.

The company Deltatre (http://www.deltatre.com/) markets a set of services operable on different media (television set, Smartphone, tablet computer, etc.) to merge different data with the video. These data come from a static or dynamic database of which the data are potentially collected, processed then added during a sports event.

The company Opta (http://www.optasports.com/) has an approach close to Deltatre or Amisco, also creates video content or web pages associating images, various statistics and videos collected in databases.

Without specifically citing the companies carrying out the technique of adding information to videos, it is common at the time of an event transmitted on televised channels to see various information added: for example when a tennis serve is viewed in slow-motion by adding the speed of the ball thereto.

The embedding of data in a video is a human operation, a person being involved to interpret the video in order to associate complementary data therein. These data do not come from sensors borne by the players and furthermore the computing power implemented as well as the time of human involvement may be very great since they are little limited by constraints of time, size, computation rapidity or energy dissipation.

As regards the merging between video and data from sensors, there may also be cited the video recording input terminals which comprise sensors (GPS receiver, temperature sensor, humidity sensor, etc.) and which associate the data from those sensors with the video or the photograph.

Other examples merging video and data come from the world of cinema in which actors have sensors which assist the director to create scenes from digitally synthesized images and videos.

None of the existing systems of the state of the art enables a user producing an enhanced video to easily interact with the filmed person or persons possessing sensors with the aim of automatically creating enhanced video sequences. The object of the invention is to provide a device including the terminal that films, the connected sensors as well as the servers for processing and storing the data in order to make the creation of enhanced videos possible and effective.

PRESENTATION OF THE INVENTION

In order to simplify the disclosure of the invention, the description is made for a case which brings together a person creating the film and controlling the terminal that generates the video and a person bearing the connected sensor or sensors. The person creating the film is designated "the director" below and the person bearing the connected sensors is designated "the sportsperson". It is obvious that this description is in no way limiting and is only used to make what is said more concrete by dealing with a specific case. By way of example, it is possible to imagine the case in which "the director" and "the sportsperson" are the same person, the terminal that records the video then being controlled by the sportsperson. It is also obvious that the person skilled in the art will know how to use the device described in fields other than the field of sport.

The disclosure lists the problems specific to the director-sportsperson interaction and provides solutions which constitute the object of the invention.

Automatic creation of videos from data supplied by the sensor or sensors: As was mentioned when the description was made of the state of the art, the existing systems are based on human involvement for detecting the fact what the sportsperson is doing at a given time in order to create a video sequence with an effect of slow-motion type, for example, which will then be distributed over the different broadcast channels (television, second screen of tablet computer type, web site, etc.). The object of the invention is in particular to authorize the automatic generation of relevant video sequences in slow-motion. The following steps describe the process:

The type of sport carried out is known the user profile is known (weight, size, key performance for the sport carried out.). This profile is either available locally on the Smartphone or retrieved from a remote service within the telecommunication network.

The director targets the start of video recording.

This triggering may also be governed remotely by the sportsperson via a remote control unit.

The different parameters coming from the sensors: acceleration, rotational speed, orientation, atmospheric pressure, are recorded at the sampling instants for the time.

The director stops the video recording. This triggering may also be controlled at a distance by the sportsperson.

Thus, after the sports sequence, the Smartphone has recorded in its memory the data relative to the video as well as the data corresponding to the activity of the sportsperson. These latter are synchronized temporally with the video. All these "video+activity" data are entered into an algorithm given the task of selecting the "highlights" of the video sequence. The "highlights" correspond to the most intense phases of activity. By way of example, the acceleration is analyzed over all the activities, the peaks are noted, if the 5 most interesting peaks are sought, 5 temporal zones will be selected. The duration of each of the zones depends on the sport carried out: of the order of 2 s for example for tennis, a duration which we will call "characteristic duration". The 5 temporal zones thus selected are sent to another algorithm which will collect the data from the videos over temporal windows centered on each of the zones and of a length (configurable) greater than the "characteristic duration" of an event, typically 2 to 3 times longer. Once these "video+ activities" data have been retrieved, the Smartphone will be capable, thanks to an appropriate program, of generating relevant slow-motion video sequences since they correspond to times of intense activity. Furthermore the data coming from the activities will be used to add information to the video such as speed, acceleration, power, seat height, etc. These data associated with the video viewed in slow-motion constitute which we call an "enhanced video" since it is enhanced with data assisting in the interpretation and appreciation of the sports performance.

The process described above corresponds to an automatic generation without the involvement of the director. It will however be possible to modify the settings in order to act on the enhanced videos sequences: If the videos do not satisfy the director, he can act on various parameters to generate other video sequences, for example by modifying the number of videos generated (modification of the "number of videos to generate" parameter) or for instance by selecting only the videos in which the sportsperson has jumped more than 1 m, for example, etc. and/or for which the power developed is greater than a certain threshold.

The principle of default parameterization enables an automatic generation of enhanced videos adapted for simplified and fast use. The modification of the default parameters (via an "expert" menu for example) will authorize the modification of the parameters for those who wish to have customized generation.

From the generation process, the following data are available:

The video data+raw activity data: raw data from the sensors

The video data+interpreted data: computed performances, for example the power developed, the effective value of acceleration over a given time, the height of a jump, etc., this being based on data from the sensors The enhanced videos: directly interpreted data embedded in the video, thus no dissociation between the video and the data Specific rights will give access to the entirety of the data cited or only to part. Given that the volume of the data varies according to the nature thereof, the interpreted data constitute a compression of the raw data.

As regards the adjustment of the slow-motion, this may be carried out with a number of images per second which will be defined according to certain parameters, for example: The video sequence is filmed at 120 images per second, the slow-motion viewing around the times of interest will be carried out at a fixed cadence of 20 images per second or else at a variable cadence varying from 120 images per second at the start of the sequence, reducing to 10 images per second during the phase of intense activity in order to reproduce as best possible the whole performance of the sportsperson, then returning to 120 images per second at the end of the sequence.

Creating photographic and video effects that are synchronized with the data from the sensors: By virtue of the data synchronized with the video, it is thus possible to automatically create instances of slow-motion according to the data from the sensors. By proceeding in similar manner, photographs extracted from the video may advantageously be created automatically too. Consider for example the case of a motorcycle jump, when the sensors have detected the peak in height at the time the jump takes place, a few photographs are extracted (4 or 5 typically) around the event. The director will next be able to select the photograph he likes the most, or even also modify the triggering criteria in order to generate other photographs. Various video or photographic effects may be created by virtue of the sensors: succession of photographs around times of intense activity, speed blur effect, specific music accompanying the time at which the sportsperson's activity is at its maximum, effects of light, luminous halo, addition of a message of congratulations, not forgetting the addition of performance information (height, time in the air—without contact with the ground or sea—, power, acceleration, speed, etc.).

Process of accelerating the processing operations consecutive to creating the video: in order to reduce the processing operations consecutive to the recording of the video enhanced with the performance data of the sportsperson, the process takes place in several steps:

Recording the video data as well as the performance data from the sensors.

Continuously checking the maximum value of certain parameters such as the acceleration, the rotational speed, or a combined quantity taking into account the instantaneous power for example. On the basis of these computations, keeping up-to-date and storing in the memory of the Smartphone (or of the connected sensor according to the case) of the temporal markers enabling the start of the 5 (configurable) most interesting sequences to be identified.

On the basis of the temporal markers, creating slow-motion video sequences over a time of 2 s (configurable) centered on the temporal markers.

Thus the processing is much faster since it is focused only on the zones of interest. The slow-motion as well as all the effects we saw earlier (addition of text, embedding of performance data, addition of a voice message, creation of a photograph at the peak performance, etc.) are only carried out over the interesting zones in order to produce as quickly as possible the enhanced video which will be viewed by the director or shared with those around him.

Creating enhanced videos from video sources that are not initially (temporally) synchronized with the sensors: In certain cases the terminal which records the video is directly temporally synchronized with the data from the sensors. This is for example the case when a Smartphone records the video while collecting the data coming from the sensors via a radio communication link. In this case the smartphone defines the time reference: on the basis of its internal clock, on a time base coming from a GPS receiver or from a temporal base receiver receiving information from a terrestrial transmitter (France Inter transmitter in France, DCF77 system in Germany, etc.), or for instance by synchronizing itself with the mobile telephone network. The Smartphone communicates with the connected sensor in order for them to synchronize their respective time bases. Of course, it is possible to imagine situations in which the sensor itself has a GPS receiver or a temporal base receiver in which case the synchronization is carried out via that time base that is common to the Smartphone and the connected sensor.

But in other cases there are no similar synchronization means to those described in the previous paragraph. This is the case in which we are interested and for which we provide a method of temporal synchronization: the sensor comprises several LEDs (light-emitting diodes) arranged so as to constitute a specific luminous graphical pattern of which the illumination is temporally controlled by the microprocessor present in the connected sensor. At the start of a session the LEDs blink in a particular way and the director is requested to point his video camera (or any other device making the recording) towards the LEDs until the blinking stops, before continuing the recording of the video. Once the video recording has been made and stored, 2 steams are generated: the video stream from the camera as well as a stream integrating the times of verification of the LEDs and the performance data coming from the sensors. These two data stream are retrieved by a computer (desk computer, portable computer, Smartphone, digital tablet, etc.) which comprises a specific program implementing a signal processing algorithm known to the person skilled in the art applied to those two streams and making it possible to temporally synchronize the two streams.

Thus, at the end of this processing, the performance data are temporally synchronized with the video data and the director or any other person will be able to create enhanced videos with automatic creation mechanisms as seen earlier. The luminous graphical pattern may also be replaced by a device generating an audible sound (small loudspeaker, generator using the piezoelectric effect—commonly called a buzzer —, etc.) which will lead to recognizing a specific audio signature instead of the graphical signature of the luminous graphical pattern. In another embodiment it may be advantageous to simultaneously record, in the terminal performing the recording of the video (and, it may be recalled, audio) and in the connected sensor (thus having a microphone and electronics required for the processing), a particular sound (users command for example) which will then serve for the temporal synchronization. This temporal synchronization is made by searching for similarities (in a portable computer for example) between the two signals: the one stored in the terminal making the video recording and the one stored in the connected sensor.

Operating modes: In a rather similar manner to that described in the paragraph "Creating enhanced videos from video sources that are not initially (temporally) synchronized with the sensors" in certain cases the Smartphone and the connected sensor or sensors are not permanently connected: The director produces the video (also recording the sound, it should be recalled) independently of the recordings of the connected sensors, the connected sensors collecting the data from the sensors, analyzing them and storing those results in a memory internal to the connected sensor. Finally there are three distinct operating modes:

A real-time mode in which the Smartphone and the connected sensor or sensors are temporally synchronized. The data from the sensors are transmitted (after local processing in the connected sensor) to the Smartphone practically in real time (the processing time being the only difference).

A deferred time mode in which the Smartphone and the connected sensor or sensors are temporally synchronized (before or after the recordings). However the data from the sensors are stored only in the internal memory of the connected sensor and are only transmitted at particular times to the Smartphone for constructing the enhanced videos. In order to establish ideas, imagine a ski descent, at the start of the descent the sportsperson activates her connected sensor. The director films the sportsperson at preferred times during the descent.

During the descent or at the end of the descent the director retrieves the data from the connected sensor in order to construct the enhanced video. At each exchange of data between the directors Smartphone and the connected sensor of the sportsperson, the temporal synchronization is carried out.

a hybrid mode corresponding to a case in which the director and the sportsperson wish to be in a real time mode. However, on account of the nature of the radiofrequency connection between the Smartphone and the connected sensor there may be times at which the connection is broken for a few seconds. In this case the connected sensor passes into deferred time mode and will send the stored (and processed) data as soon as it can to the Smartphone.

Optimization of the consumed power according to the sport played and the quality of the wireless link between the sensor or sensors and the Smartphone: the sensor is required to be miniaturized and for this consume as little energy as possible in order to carry with it a battery of small size. Devices for transmission of voice are already known which adapt the compression rate to the quality of the communication link, this being in order to transmit voice even if the quality of the link degrades. Here we have another concern which is to be added to the known principles: send information so as to optimize the consumption by the connected sensor. For this a mathematical model for connected sensor consumption is established and implemented in a program of the microprocessor contained in the connected sensor, this program continually evaluates whether it is better to perform the computations on the sensor or to perform them remotely on the Smartphone for a maximum reduction in the energy consumption of the connected sensor. The operation is explained later in the part "Description of the figures and of the embodiments".

"General public" and "professional" configuration, implications: in the interest of simplification the description made earlier corresponds to the case referred to as general public implementing a Smartphone and one or more connected sensors. The described device may also operate in what is referred to as a professional configuration, in this case the connected sensor or sensors communicate not with a Smartphone but with a unit carried on the body or on an item of equipment of the sportsperson, this unit is given the task of collecting and processing the data from the connected sensors before transmitting them over a greater distance than the Smartphone-connected sensor link is able to do. The unit in question may also comprise sensors and as this unit is only adapted to collect, process and transmit the information from the connected sensors it does not necessarily have to include a camera, a screen or a very powerful processor, it is thereby substantially lighter and less bulky than a conventional Smartphone.

DESCRIPTION OF THE FIGURES AND EMBODIMENTS

FIG. 1: the wrist band (1) is a connected sensor as defined earlier, it comprises a certain number of electronic components as well as sensors. The electronics integrated into the wristband comprises radio communication means adapted to exchange information with the Smartphone (3). The radio communication link (2) between (1) and (3) is symbolized in the drawing. The product which comprises the sensors is here represented in the form of a wristband, this is in no way limiting, there are other configurations such as a small product unit that can be housed in a holding accessory (at various locations on the body) without electronics, or for instance a very flat and deformable product in order to adapt to the shapes of the body. As was seen earlier in the disclosure, the Smartphone retrieves the data coming from the sensors in order to exploit them to produce the enhanced videos.

Figure 2:
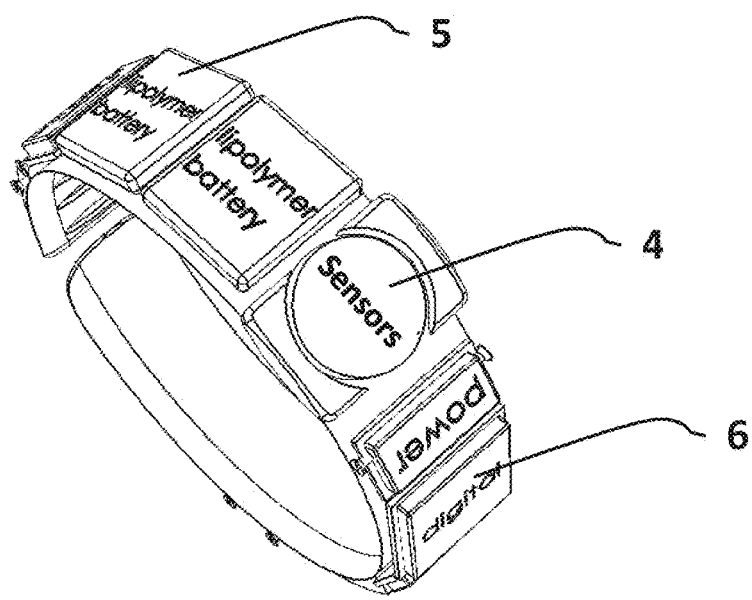

FIG. 2: This Figure represents an internal view of the wristband. The sensors (4) call upon various technologies such as MEMS (Micro-Electro-Mechanical Systems) technology enabling considerable miniaturization and reduced consumption. The wristband also comprises a rechargeable battery (5) as well as a set of electronic components (6) of microprocessor type and integrated circuits for radio communication. The radio communication standard used for the link (2) may, for example, be of the BLE (Bluetooth Low Energy) type, or of Wifi type (IEEE standard 802.11). The sensors (4) send their information to the microprocessor which merges those data in order to compute different parameters such as speed using a simple integration, the displacement using a double integration, and for instance changes in orthogonal frames of reference, etc. this being before sending those data to the radio communication emitter which will send them to the Smartphone.

Figure 3:
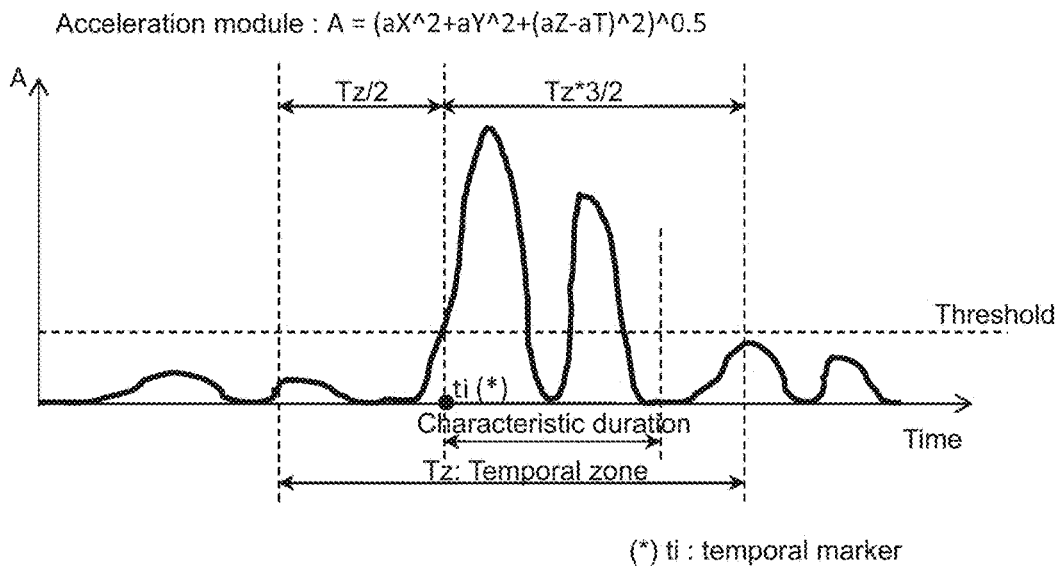

FIG. 3: this Figure illustrates the descriptions given above, in particular as regards lines 10 to 35 of page 5. The axis for the abscissae represents time which makes it possible to identify the instants at which the information from the different sensors is recorded. The axis for the ordinates represents the acceleration A. aX represents the acceleration along the X-axis, aY that along the Y-axis and aZ that along the Z-axis. aT is the terrestrial acceleration along the Z-axis, also measured using sensors in static phases. ti is the temporal marker corresponding to the instant at which the acceleration module exceeds a predefined threshold which makes it possible to define a phase of intense activity named "highlight". A temporal window named "Temporal zone" of duration Tz is placed in register with the temporal marker ti. This temporal window is adjusted so as to be greater than the characteristic duration of an activity (tennis serve, boxing punch, etc.) of the sport carried out.

Figure 4:
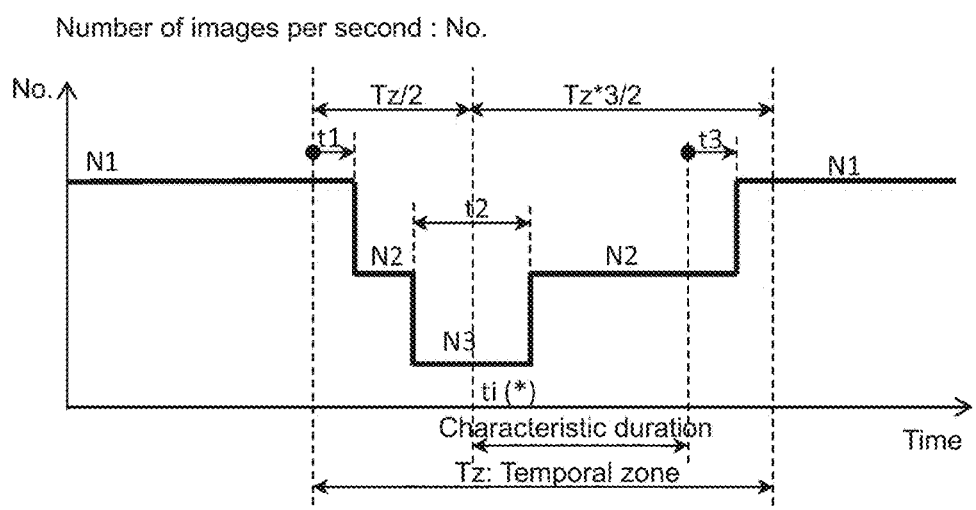

FIG. 4: This Figure is directly dependent on FIG. 3 since all the temporal markers are deduced therefrom. This graph shows how the number of images per second of the video is made variable in order to better appreciate the slow-motion: N1 is typically equal to 120 images per second, N2 equal to 10 images per second and N3 equal to 5 images per second. In order to make matters clear, for tennis for example we will have the following values: Characteristic duration 2 seconds, Tz=4 seconds; t1=0.5 second; t2=1 second; t3=0.5 second.

Figure 5:
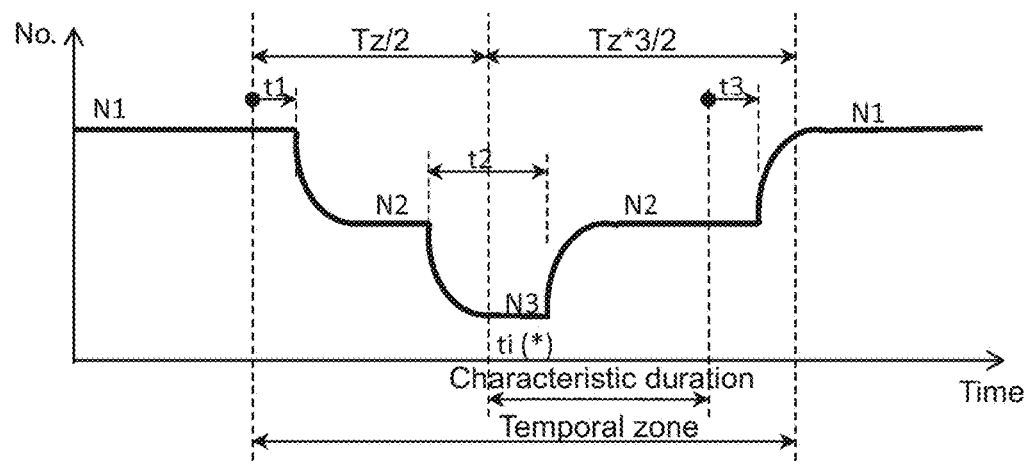

FIG. 5: This is a real variation which will be applied in order to make the changes more progressive. This curve is obtained by low-pass filtering, of the second order for example, based on the curve of FIG. 4.

Figure 6:
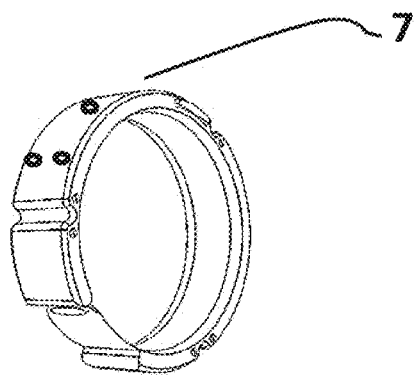
Figure 7:
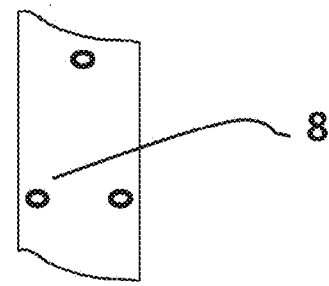

FIGS. 6 and 7: These Figures represent the wristband (7) integrating sensors to which has been added the luminous graphical pattern described above in the paragraph "Creating enhanced videos from video sources that are not initially (temporally) synchronized with the sensors". FIG. 7 represents the local detail of the graphical pattern composed of 3 luminous points, each luminous point being an identical LED (8). This very simple graphical pattern in this example may be more complex and represent lines, a letter for example, etc.

The objective of the processing for pattern recognition (not described here as already known to the person skilled in the art) is to determine at what instant that pattern disappears in order to perform the temporal synchronization. Of course, the accuracy is limited by the sampling frequency of the successive images recorded by the camera: 100 images per second for example. With the aim of facilitating this synchronization, the wearer of the wristband may vocally control (microphone and electronics of course necessary in the sensor) the instant at which the LEDs start operating, thus the user will be able to take care to have available the camera of the terminal making the recording adequately in order for the luminous pattern to be properly in the camera's field of shooting. This vocal triggering may also be achieved by vibratory triggering, the wearer of the "sensor" tapping on the body of the "sensor" in a particular way. Advantageously, it is possible to combine this device for luminous pattern recognition with a vocal recognition device exploiting a simultaneous recording of the sound in the sensor and in the terminal making the video (and audio) recording.

Figure 8:
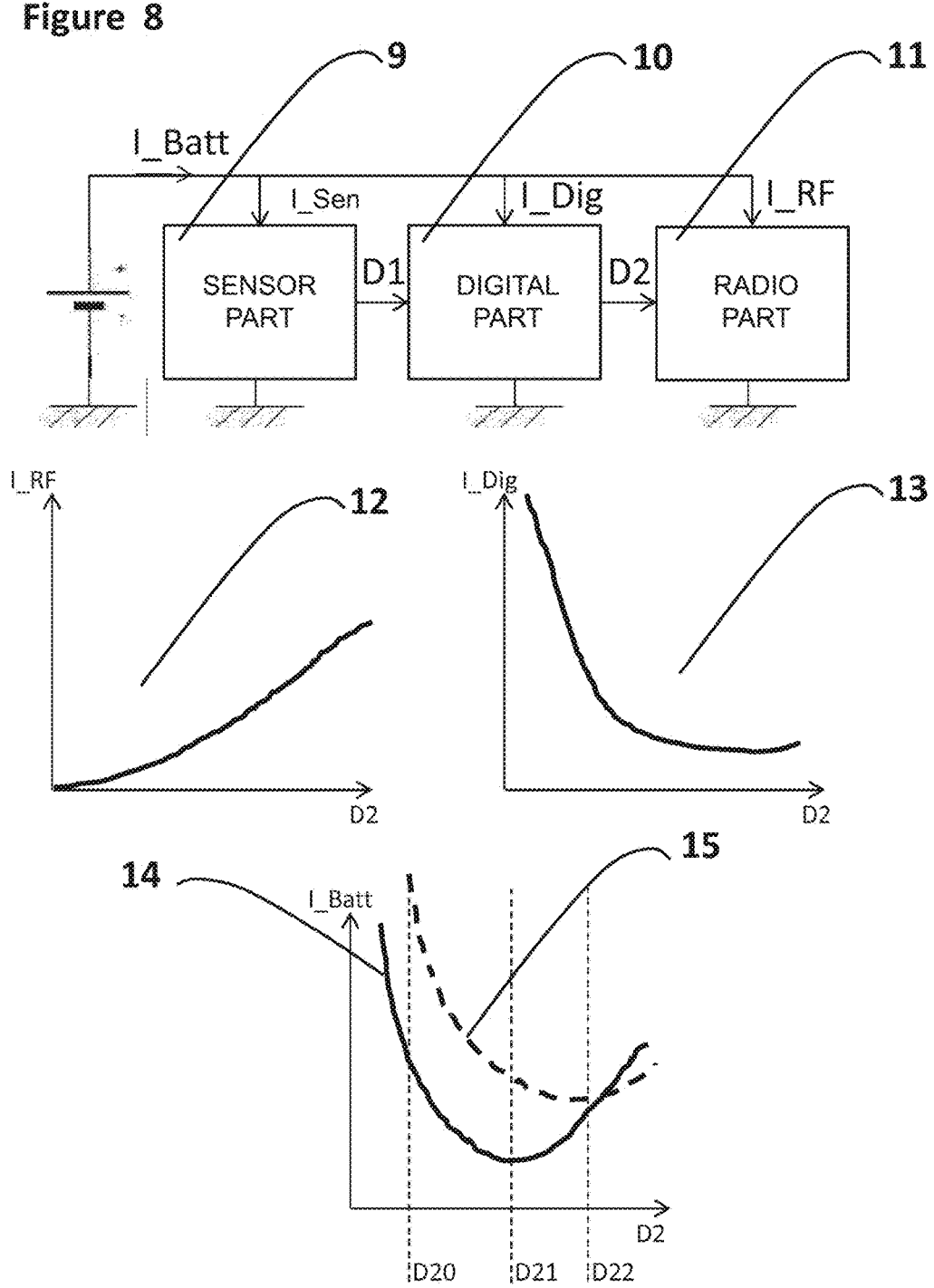

FIG. 8: These Figures describe the functional blocks of the connected sensor in a simplified way. Block (9) represents the sensors consuming a current I_Cap. Block (10) represents the digital part (analog/digital converters, microprocessor, signal processing unit, memory, etc.) processing the information. This block (10) consumes a current denoted I_Dig. Block (11) represents the radio frequency part (digital/analog converters, frequency synthesizers, oscillator, amplifier, mixers, modulators, antennae, etc.) given the task of sending and receiving information at high frequency (typically at 2.4 GHz). This block (11) consumes a current denoted I_FR. At the output from block (9) the average bitrate per second (denoted bps or kbps=kilobit per second) is denoted D1. It is denoted D2 at the output from block (10), that same bitrate being found again at the input to block (11). The curve (12) represents the typical change in the current consumed by the radio frequency part according to the rate D2. This curve is in reality a network of curves since the modulation system may be different for the same rate. In order to simplify the disclosure a single curve is represented: for the same modulation, the same level of power, etc. an increase in the average rate leads to having to transmit more often (system with temporal multiplexing) and thus leads to consumption which increases with the average rate. The curve (13) represents the typical change in the current according to D2, it is easy to understand that the more the rate reduces, the more this requires computation power to exploit the signal redundancies. In reality, this is a discontinuous curve since only some rates are possible according to the type (limited in number) of algorithm applied. In order to simplify the disclosure a continuous curve has been represented. Curve (14) represents the appearance of the total current drawn from the battery for a given configuration and curve (15) for another configuration, indeed the processing operations are different according to the sport and the type of modulation chosen at a given time.

The connected server continuously performs an analysis according to various criteria (modulation in course, type of sport, types of digital processing operations available, etc.) in order to choose the best compromise and thus decide whether the processing operations are carried out locally in the connected sensor or in the Smartphone, example for a few cases by referring to curves (14) and (15):

First case: The quality of the radio frequency link (2) is such that it is possible to send at the rate D22. In the case of curve (14) it is necessary to send at rate D21 in order to optimize the consumption of the connected sensor whereas in the case of curve (15) it is advantageous to send at the rate D22 and thus choose the appropriate type of digital processing.

Second case: The quality of the link (2) is such that it is only possible to send at the rate D20. In the case of curve (14) it is necessary to send at the rate D20 and the same will apply for the case of curve (15).

As regards the processing operations which lead to different rates D2, we can have the following configurations:

Practically no processing in the connected sensor, the data from the sensors being simply collected then sent to the radio block of the connected sensor, in this case the rate D2 is a maximum, 30 kbps for example and the analysis processing detailed is carried out by the Smartphone.

A processing operation consisting of performing any analysis of the data and of detecting, for a given sport, the type of action and its characteristics. For example, "serve performed with a maximum acceleration of 5 g and a rotational speed of 600 degrees per second". In this case, it is obvious that the rate necessary to code that information will be very limited, the rate D2 will be very low, 300 bps for example. In this case, the processing is very limited as regards the Smartphone.

In an extreme case we will have cases in which the processing carried out in the connected sensor will not enable it to send the information in real time. Take for example the case of a maximum authorized rate D2 (to maintain the connected sensor-Smartphone connection) of 200 bps, if the minimum which the connected sensor knows how to attain via its digital processing (given its limited computing power) is 400 bps this will lead to transmission delay.

In another example leading to an intermediate rate D2, the connected sensor analyzes its positioning in space which it models with a curve that is parameterized (using a polynomial formulation for example) then sends the values of those parameters. In this case the rate will be of the order of 5 kbps and the Smartphone will have to perform complementary processing operations of data analysis.

Figure 9:
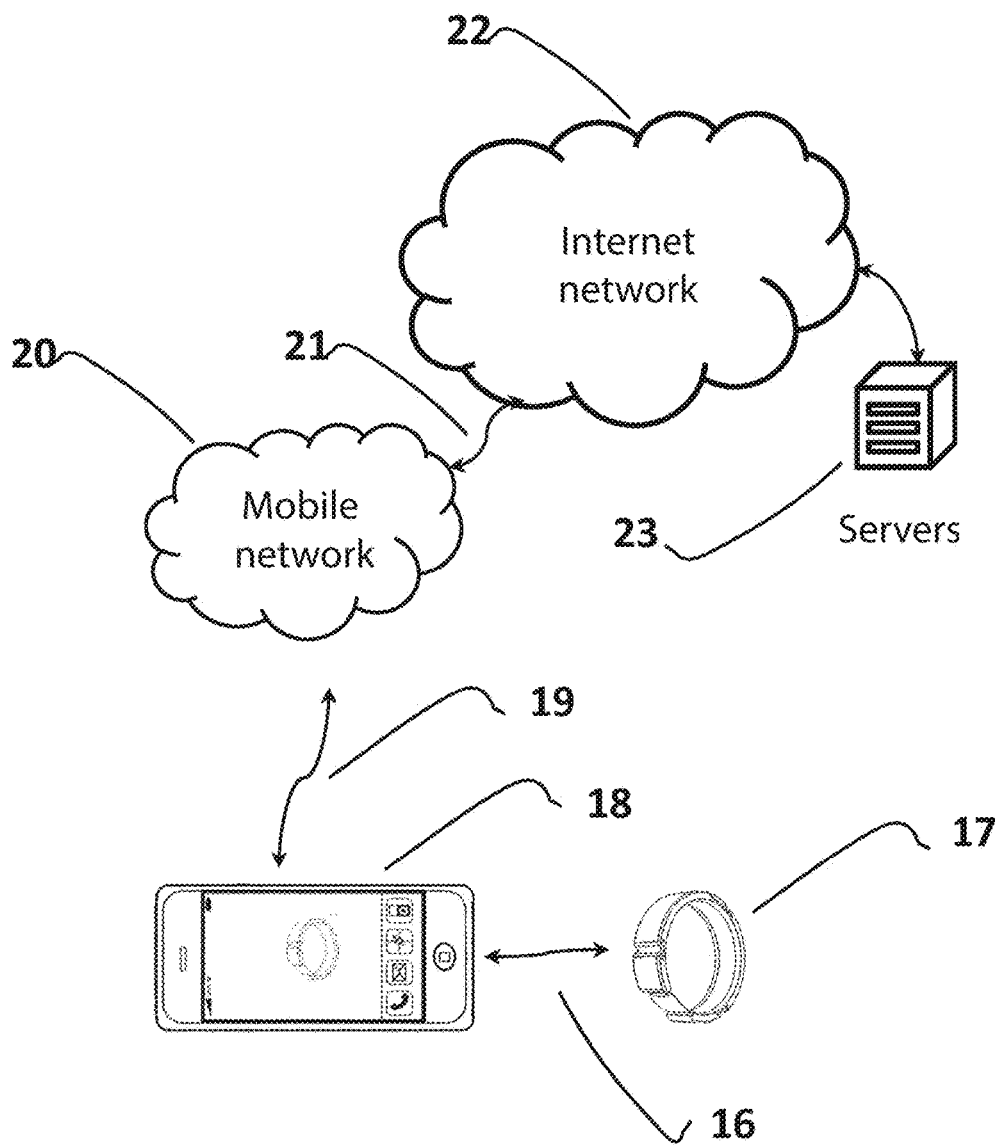

FIG. 9: This Figure gives a general representation of what is referred to as the general public system. A connected sensor or sensors (17) communicating via the radio frequency link (16) with the Smartphone (18), itself communicating with the mobile telephone network (20) via a radio frequency link (of 2G, 3G, 4G, etc. type) to send for example enhanced videos or connect itself with the server to retrieve or store data relative to the sportsperson or simply store the data from the sensors. The mobile network is interconnected with the internet network (22) making it possible to access the data servers (23) also linked to the internet network.

Figure 10:
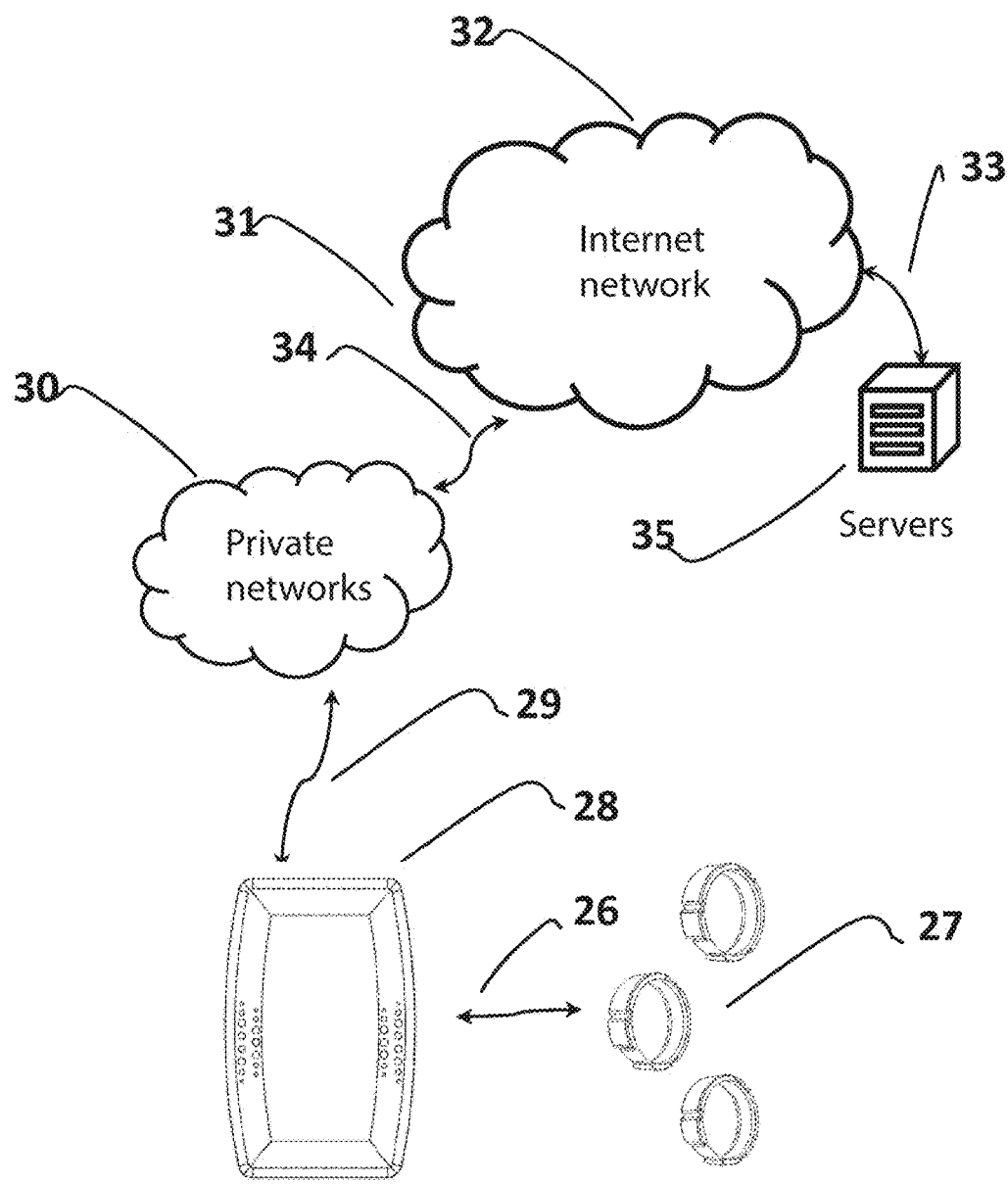

FIG. 10: relative to FIG. 9 the smartphone is replaced by a unit (28) given the task of communicating with the connected sensor or sensors. The link (26) is preferably identical to that of FIG. 9 (link (16)). The unit (28) also comprises sensors, there are thus scenarios in which the connected sensors (27) are not necessary. The case may for example be cited of rugby in which for certain matches the unit (28) will be placed between the shoulder blades of the sportsperson without addition of other sensors of type (27). Unit (28) communicates using a link (29) of radio frequency type with a private network (30) in order to transmit the data coming from the sensors. The link (29) uses for example what are referred to as the ISM (Instrumentation, Scientific and Medical) frequencies with a proprietary protocol for connection to a first private network comprised in (30) itself constituted by several fixed radio frequency stations. In the case of a football match for example each player is equipped with a unit and several connected sensors, these units (28) communicating with radio frequency stations situated around the turf between the spectators and the area of play. The fixed stations forming part of the private network are linked for example via an Ethernet network to a second private network situated in (30) typically linked to the lorries serving to carry out the television production and which collect and control the cameras filming a sports event. Thus the data from the sensors and from the cameras can be merged (as this is done in the Smartphone) to create the enhanced videos. The private networks (30) may be linked to an Internet network in order to access servers or more simply in order for the set to be remotely controlled. In a variant the data from the sensors are sent and stored in servers (35), these data are then retrieved by the lorries serving to perform the television production via their private network. The enhanced videos may thus be created.

The invention claimed is:

1. A system for creating enhanced videos, comprising:
   a set of sensors, each sensor comprising:
      means for capturing raw data,
      means for computing interpreted data based on raw data, and
      radio communication means for transmitting data to a terminal; and
   a terminal comprising:
      video capture means for capturing a video,
      radio communication means for receiving data transmitted by the sensors,
      means for synchronizing interpreted data and captured video, and
      means for automatically generating video sequences from the captured video comprising synchronized embedding of the interpreted data,
   wherein the means for automatically generating video sequences comprise means for generating a slow-motion video sequence, a cadence of the slow-motion video sequence depending on the data from the sensors,
   wherein the terminal further comprises means for computing interpreted data from raw data, and
   wherein each sensor further comprises:
      means for determining a quality of a radio link between the sensor and the terminal, and
      means for analyzing electrical consumption of the sensor, according to diverse criteria comprising modulation in course of the radio communication and types of digital processing, using a digital model of consumption, in order to select a best compromise of distribution of processing operations between i) the means for computing interpreted data within the sensor and ii) the means for computing interpreted data of the terminal, to limit the electrical consumption of said sensor.

2. The system according to claim 1, wherein:
   the means for automatically generating video sequences comprise means for extracting photographs from the video on basis of the data from the sensors.

3. The system according to claim 1, wherein:
   the means for automatically generating video sequences comprise means for creating video or photographic effects on basis of the data from the sensors.

4. The system according to claim 3, wherein:
   said effects are chosen from:
      extraction of a succession of photographs around instants of intense activity;
      speed blur effects;
      effects of light;
      luminous halo effects; and
      addition of specific music.

5. The system according to claim 2, wherein:
   the means for automatically generating video sequences comprise means for creating video or photographic effects on basis of the data from the sensors.

* * * * *